US012557998B2

(12) United States Patent
 Doelman et al.

(10) Patent No.: US 12,557,998 B2
(45) Date of Patent: Feb. 24, 2026

(54) DERIVATION OF HEARTBEAT INTERVAL FROM REFLECTION SIGNAL

(71) Applicant: Neteera Technologies LTD., Jerusalem (IL)

(72) Inventors: Reinier Doelman, Jerusalem (IL); Ehud Fishler, Shoham (IL)

(73) Assignee: Neteera Technologies LTD., Jerusalem (IL)

( * ) Notice: Subject to any disclaimer, the term of this patent is extended or adjusted under 35 U.S.C. 154(b) by 0 days.

(21) Appl. No.: 18/718,093

(22) PCT Filed: Dec. 21, 2022

(86) PCT No.: PCT/IL2022/051365
§ 371 (c)(1),
(2) Date: Jun. 11, 2024

(87) PCT Pub. No.: WO2023/119285
PCT Pub. Date: Jun. 29, 2023

(65) Prior Publication Data
US 2025/0120602 A1 Apr. 17, 2025

(30) Foreign Application Priority Data
Dec. 23, 2021 (IL) .......................................... 289321

(51) Int. Cl.
A61B 5/024 (2006.01)
A61B 5/00 (2006.01)
(Continued)

(52) U.S. Cl.
CPC ...... A61B 5/02444 (2013.01); A61B 5/02405 (2013.01); A61B 5/0507 (2013.01);
(Continued)

(58) Field of Classification Search
CPC ..... A61B 5/0507; A61B 5/1102; A61B 5/726; A61B 5/02444; A61B 5/02405;
(Continued)

(56) References Cited

U.S. PATENT DOCUMENTS

2003/0135097 A1* 7/2003 Wiederhold ....... A61B 5/02405
600/509
2013/0109989 A1* 5/2013 Busse .................... A61B 5/029
600/527
(Continued)

FOREIGN PATENT DOCUMENTS

CN 111657889 A 9/2020
WO 2018167777 A1 9/2018
(Continued)

OTHER PUBLICATIONS

Malesevic [Contactless Real-Time Heartbeat Detection via 24 GHz Continuous-Wave Doppler Radar Using Artificial Neural Networks, Sensors 2020, 20(8), 2351] (Year: 2020).*
(Continued)

*Primary Examiner* — Oommen Jacob
(74) *Attorney, Agent, or Firm* — Renner, Otto, Boisselle & Sklar, LLP

(57) ABSTRACT

Method and system for deriving interbeat interval (IB1) measurement of subject. A radar device receives a reflection radar signal reflected from subject. A signal portion of reflection radar signal at a range of subject is extracted, the signal portion collected over predefined intervals and consisting of an in-phase component and a quadrature component. The signal portion is filtered by applying a complex valued continuous wavelet transform (CWT) to derive a time domain ballistocardiograph (BCG) signal with cyclically repeating features, such that the time displacement between repeating features of the derived BCG signal is representative of a first heartbeat interval measurement of (Continued)

subject. At least one segment of the BCG signal over a selected time duration may be identified using a matrix profile technique, such that the time displacement between successive identified segments is representative of a second heartbeat interval measurement. Radar signal may be THz/millimeter-wave and FMCW radar signal.

15 Claims, 7 Drawing Sheets

(51) Int. Cl.
| | | |
|---|---|---|
| *A61B 5/0507* | (2021.01) | |
| *A61B 5/11* | (2006.01) | |
| *A61B 5/319* | (2021.01) | |

(52) U.S. Cl.
CPC .......... *A61B 5/1102* (2013.01); *A61B 5/1126* (2013.01); *A61B 5/725* (2013.01); *A61B 5/7257* (2013.01); *A61B 5/726* (2013.01); *A61B 5/7278* (2013.01); *A61B 5/319* (2021.01)

(58) Field of Classification Search
CPC ..... A61B 5/1126; A61B 5/725; A61B 5/7257; A61B 5/7278; A61B 5/319; A61B 5/7225; A61B 5/024
See application file for complete search history.

(56) References Cited

U.S. PATENT DOCUMENTS

| | | | | |
|---|---|---|---|---|
| 2017/0273635 A1* | 9/2017 | Li | ......................... | A61B 5/7278 |
| 2020/0113459 A1* | 4/2020 | Jäntti | ..................... | G16H 50/20 |
| 2020/0386879 A1 | 12/2020 | Shouldice et al. | | |
| 2023/0014336 A1* | 1/2023 | Shin | ....................... | A61B 5/024 |
| 2025/0120602 A1* | 4/2025 | Doelman | ............. | A61B 5/7257 |

FOREIGN PATENT DOCUMENTS

| | | | | | |
|---|---|---|---|---|---|
| WO | WO-2020012455 A1 * | 1/2020 | | .............. | A61B 5/18 |
| WO | 2021118602 A1 | 6/2021 | | | |

OTHER PUBLICATIONS

Tomii [Heartbeat Detection by Using Doppler Radar with Wavelet Transform Based on Scale Factor Learning, IEEE ICC 2015 SAC—Communications]. (Year: 2015).*

Ebrahim [Blood Pressure Estimation Using On-body Continuous Wave Radar and Photoplethysmogram in Various Posture and Exercise, Scientific Reports | (2019) 9:16346 | ] (Year: 2019).*

Li [Wavelet-Transform-Based Data-Length-Variation Technique for Fast Heart Rate Detection Using 5.8-GHz CW Doppler Radar, IEEE Transactions On Microwave Theory and Techniques, vol. 66, No. 1, Jan. 2018] (Year: 2018).*

Guohua [Study of the Ballistocardiogram signal in life detection system based on radar, Proceedings of the 29th Annual International Conference of the IEEE EMBS Cité Internationale, Lyon, France, 2007 ] (Year: 2007).*

Examination Report issued for related Australian National Stage Application No. 2022417663, mailed Aug. 28, 2024.

Guohua, Lu et al., "Study of the Ballistocardiogram signal in life detection system based on radar", Proceedings of the 29th Annual International Conference of the IEEE EMBS, Lyon, France (2007).

Wang, JQ, et al., "The study on non-contact detection of breathing and heartbeat based on radar principles", Chinese Journal of Medical Instrumentation, 25 (3): 132-135, (2001). (Only Abstract Provided).

Fatisson, Julien, et al. Influence diagram of physiological and environmental factors affecting heart rate variability: an extended literature overview; Heart International: Sep. 16, 2016.

Ebrahim, Malikeh Pour, et al. Blood Pressure Estimation Using On-body Continuous Wave Radar and Photoplethysmogram in Various Posture and Exercise Conditions; Scientific Reports 9:16346 (2019). https://doi.org/10.1038/s41598-019-52710-8.

Tsipouras, M. G., et al. An arrhythmia classification system based on the RR-interval signal; Artificial Intelligence in Medicine: vol. 33, Issue 3, pp. 237-250, Mar. 2015.

International Search Report and Written Opinion issued for priority international application No. PCT/IL2022/051365, mailed Mar. 30, 2023.

* cited by examiner

130

132

134

136

138

DERIVATION OF HEARTBEAT INTERVAL FROM REFLECTION SIGNAL

This application is a National Phase application filed under 35 U.S.C. § 371 of PCT International Application No. PCT/IL2022/051365 with an International Filing Date of 21 Dec. 2022, which claims priority to Israel Application No. 289321, filed on 23 Dec. 2021.

FIELD OF THE INVENTION

The present invention generally relates to the fields of heart rate variability estimation, temporal signal processing, and machine learning analyses.

BACKGROUND OF THE INVENTION

The cardiac cycle defines a sequence of alternating contractions and relaxations of the heart between successive heartbeats to enable the pumping of blood throughout the body. The time interval between consecutive heartbeats, also known as an "interbeat interval (IBI)", normally varies from heartbeat to heartbeat during regular cardiac operation but may tend toward uniformity under certain conditions. Heart rate variability (HRV) is a parameter describing the fluctuation in the interbeat interval values. HRV can be computed from "R-R intervals" between successive "R" points corresponding to peaks of the QRS-complex in an electrocardiogram waveform signal. HRV statistics may serve as indicators for various physiological and pathological factors, such as: cardiovascular disease (e.g., myocardial infarction); neurological disorders; lifestyle habits (e.g., physical activity, alcohol consumption); physical attributes (e.g., age); neurophysiological issues (e.g., stress, fatigue, depression); and cardiac irregularities (e.g., cardiac arrhythmia).

Heartbeat detection is typically performed using an electrocardiograph or electrocardiogram (ECG) machine, which measures the electrical activity of the heart. However, this requires traveling to a dedicated healthcare facility and undergoing discomforting adhesion of multiple electrodes and cables on body parts (usually the chest or limbs) for obtaining an ECG waveform. A qualified practitioner or clinician is needed to implement proper positioning of the electrodes and to operate the ECG machine. Heartbeats may also be derived from photoplethysmography (PPG) measurements, which uses optical measurement techniques to monitor volumetric variations in blood circulation. PPG measurements are obtained by illuminating the skin with a light source and then measuring the changes in reflection or absorption of the light with a photodetector, such as by means of a pulse oximeter. Yet such devices usually require components to be in physical contact with a body part of the subject, such as being attached to a finger. There also exist wearable devices, such as smartwatches or chest straps, which incorporate smaller sensors configured to obtain heart rate or cardiac cycle information. However, these wearable heart monitoring devices are often cumbersome and prone to malfunctions and inaccuracies. Moreover, these devices must operate under adequate lighting conditions and must have a direct line-of-sight with clear visibility to the measured skin region. Thus, they cannot function under low light or poor visibility conditions, or through obstructions or occlusions, such as clothing worn by the subject.

Publications describing heartbeat detection and heart rate variability include: Fatisson, J., Oswald, V., & Lalonde, F. (2016). Influence Diagram of Physiological and Environmental Factors Affecting Heart Rate Variability: An Extended Literature Overview. *Heart International,* 11(1); Pour Ebrahim, M., Heydari, F., Wu, T. et al. (2019). Blood Pressure Estimation Using On-body Continuous Wave Radar and Photoplethysmogram in Various Posture and Exercise Conditions. *Sci Rep* 9, 16346; and Tsipouras, M. G., Fotiadis, D. & Sideris, D. (2015). An arrhythmia classification system based on the RR-interval signal. *Artificial Intelligence in Medicine,* 33(3), 237-250.

U.S. Patent Application No. 2020/0386879 to Shouldice et al, entitled: "Detection and identification of a human from characteristic signals", discloses a physiological parameter monitoring system for human identification and authentication. One or more processors may be configured to process signals from one or more sensors to identify a person. The processing may include evaluating features from the signals such as breathing rate, respiration depth, degree of movement and heart rate. The sensors may be radio frequency non-contact sensors with automated detection control to change detection control parameters based on the identification of living beings, such as to avoid sensor interference.

China Patent Application Publication CN 111657889A (Univ Dalian Tech), entitled: "Non-contact driver fatigue detection method based on millimeter-wave radar", is directed to the use of millimetre-wave radar to collect physiological information and establish a general fatigue state detection model. Collected thoracic cavity vibration signals are tracked with a designated phase, and extracted, unwound, and bandpass filtered. The heart rate signal is separated from the respiratory signal, and a wavelet transform is used to calculate respective time-frequency domain values of the two physiological signals, to obtain heartbeat frequency and respiratory frequency. Heartbeat frequency and heart rate variability are calculated from the separated heartbeat signal, and derived diversity parameters are calculated according to the heart rate variability. Breathing frequency is calculated according to the separated breathing signal, and then the breathing frequency-derived diversity parameters. Selected physiological characteristics are determined, regularity of parameters are found, and statistical methods are applied to determine time of fatigue.

SUMMARY OF THE INVENTION

In accordance with one aspect of the present invention, there is thus provided a method for deriving at least one interbeat interval (IBI) measurement of at least one subject. The method includes the procedures of receiving a reflection radar signal reflected from the subject, and extracting a signal portion of the reflection radar signal at a range of the subject, the signal portion collected over predefined time intervals and consisting of an in-phase (I) component and a quadrature (Q) component. The method further includes the procedure of filtering the signal portion by applying a complex valued continuous wavelet transform (CWT) to derive a time domain ballistocardiograph (BCG) signal with cyclically repeating features, such that the time displacement between repeating features of the derived BCG signal is representative of a first heartbeat interval measurement of the subject. The method may further include the procedure of identifying at least one segment of the BCG signal over a selected time duration using a matrix profile technique, such that the time displacement between successive identified segments is representative of a second heartbeat interval measurement of the subject. The method may further include the procedure of processing the BCG signal by at least one processing step of: applying a complex number to real number mapping; removing a baseline using a high-pass filter; and/or applying a gain control function. The radar signal may be obtained using a remote non-invasive radar device that includes at least one radar transmitter, configured to transmit a radar signal to a body tissue of the subject, and at least one radar receiver, configured to receive a reflection of the transmitted radar signal reflected from the body tissue of the subject. The radar signal may be a THz or millimeter-wave radar signal. The radar signal may be a frequency-modulated continuous-wave (FMCW) radar signal. Extracting a signal portion of the reflection radar signal at a range of the subject may include applying a fast Fourier transform (FFT) to the FMCW radar signal. The method may further include the procedure of deriving a heartrate variability (HRV) measurement of the subject from a plurality of heartbeat interval measurements extracted from the BCG signal. The method may further include the procedure of converting the BCG signal into a corresponding electrocardiogram (ECG) signal and providing a visually representation thereof.

In accordance with another aspect of the present invention, there is thus provided a system for deriving at least one interbeat interval (IBI) measurement of at least one subject. The system includes a device, configured to receive a reflection radar signal reflected from the subject. The system further includes a processor, configured to extract a signal portion of the reflection radar signal at a range of the subject, the signal portion collected over predefined intervals and consisting of an in-phase (I) component and a quadrature (Q) component, and to filter the signal portion by applying a comlex vald continuous wavelet transform (CWT) derive a time domain ballistocardiograph (BCG) signal with cyclically repeating features, such that the time displacement between repeating features of the derived BCG signal is representative of a first heartbeat interval measurement of the subject. The processor may be further configured to identify at least one segment of the BCG signal over a selected time duration using a matrix profile technique, such that the time displacement between successive identified segments is representative of a second heartbeat interval measurement of the subject. The processor may be further configured to process the BCG signal by at least one processing step of: applying a complex number to real number mapping; removing a baseline using a high-pass filter; and/or applying a gain control function. The radar signal may be obtained using a remote non-invasive radar device that includes at least one radar transmitter, configured to transmit a radar signal to a body tissue of the subject, and at least one radar receiver, configured to receive a reflection of the transmitted radar signal reflected from the body tissue of the subject. The radar signal may be a THz or millimeter-wave radar signal. The radar signal may be a frequency-modulated continuous-wave (FMCW) radar signal. Extracting a signal portion of the reflection radar signal at a range of the subject may include applying a fast Fourier transform (FFT) to the FMCW radar signal. The processor may be further configured to derive a heartrate variability (HRV) measurement of the subject from a plurality of heartbeat interval measurements extracted from the BCG signal. The system may further be configured to convert the BCG signal into a corresponding electrocardiogram (ECG) signal and provide a visually representation thereof.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

The present invention overcomes the disadvantages of the prior art by providing a method and system for obtaining interbeat interval (IBI) or beat-to-beat interval (BBI) measurements with a high degree of accuracy, in a contact free manner, and without requiring professional supervision or engagement of the subject with a cumbersome and costly ECG machine. The disclosed system and method involve applying a continuous wavelet based linear filtering to a received reflection signal, such as a reflected millimeter-wave radar signal, reflected from the subject, to produce a ballistocardiogram signal representative of cardiac activity, from which an accurate heartbeat measurement (IBI) may be derived along with heartrate variability statistics. The accuracy of the derived heartbeat measurement may be further enhanced by applying a matrix profile technique to identify individual segments of the ballistocardiogram signal. The disclosed system and method may allow real-time determination of heartbeat variability parameters which can provide early indications of various physiological conditions of the subject with a high degree of accuracy, delivering reliable healthcare monitoring utilizing minimal resources.

The terms "user" and "operator" are used interchangeably herein to refer to any individual person or group of persons using or operating the method or system of the present invention, such as a person implementing a heartbeat interval measurement of a selected subject.

The terms "subject" and "living subject" are used interchangeably herein to refer to an individual upon which the method or system of the present invention is operated upon, such as a person from whom a heartbeat interval measurement is obtained. The subject may be any living entity, such as a person, human or animal, characterized with a functioning heartbeat associated with a cardiac cycle of its heart.

The terms "interbeat interval (IBI)"; "beat-to-beat interval (BBI)"; and "heartbeat interval" as used herein refer to the time interval between consecutive heartbeats of a heart.

The term "heart rate variability (HRV)" as used herein refers to the variation or fluctuation in the time intervals between consecutive heartbeats, i.e., the fluctuation of IBI values over time.

The term "repeatedly" as used herein should be broadly construed to include any one or more of: "continuously", "periodic repetition" and "non-periodic repetition", where periodic repetition is characterized by constant length intervals between repetitions and non-periodic repetition is characterized by variable length intervals between repetitions.

Figure 1:
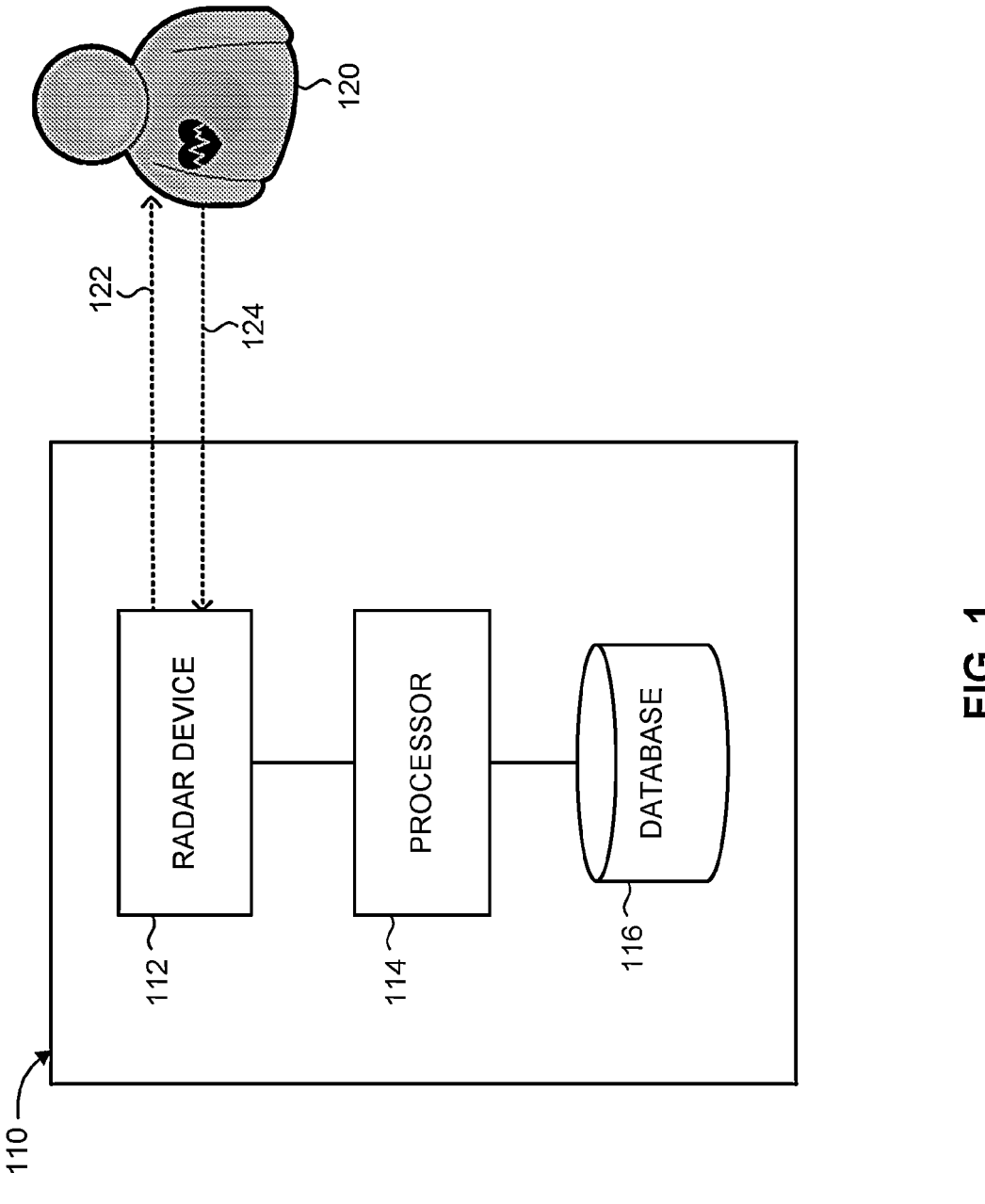
FIG. 1 is a schematic illustration of a system for deriving an inter-beat interval measurement, constructed and operative in accordance with an embodiment of the present invention.

Reference is now made to FIG. 1, which is a schematic illustration of a system, generally referenced 110, for deriving an interbeat interval measurement, constructed and operative in accordance with an embodiment of the present invention. System 110 includes a radar device 112, a processor 114, and a database 118. Processor 114 is communicatively coupled with radar device 112 and with database 118.

Radar device 112 is configured to transmit a radar signal 122 to a body part of subject 120, such as the chest or the back of subject 120, and to receive back a reflected radar signal 124. The transmitted radar signal 122 is at a sufficiently high frequency to ensure that the signal is reflected and not absorbed by the body tissue, for example in the millimetre-wave frequency band (corresponding to EHF radio frequencies). According to an embodiment of the present invention, the transmitted and reflected radar signals 122, 124 may be in the Terahertz (THz) frequency band, where the term "Terahertz (THz)" as used herein encompasses Terahertz and sub-Terahertz radiation corresponding to sub-millimeter and millimeter wave radiation, such as electromagnetic waves within the frequency band between 0.03 to 3 THz, corresponding to radiation wavelengths between 10 mm to 0.1 mm. More generally, any type of signal capable of measuring high frequency movement of body tissue representative of cardiac activity (i.e., at a sufficiently high resolution and minimal noise) may be utilized in accordance with the disclosed invention, including non-radar signals (such as, for example, laser signals). Nevertheless, the operation of the disclosed system and method will be discussed herein in the context of radar signals for exemplary purposes.

Radar device 112 may be as described for example in PCT application publication WO2018/167777A1 to Neteera Technologies, entitled "Method and device for non-contact sensing of vital signs and diagnostic signals by electromagnetic waves in the sub terahertz band", and PCT application publication WO2020/012455A1 to Neteera Technologies, entitled "A sub-THz and THz system for physiological parameters detection and method thereof". It is noted that radar device 112 operates in a contactless manner, which transmits and receives radar signals remotely without requiring a device component to be in direct physical contact with subject 120 or to be worn or attached to subject 120. It is further noted that radar device 112 may transit and/or receive a reflected signal from any direction of subject 120, such as from in front or behind or from a non-orthogonal angle relative to subject 120. Moreover, radar device 112 may transmit and receive a reflected radar signal in low light or poor visibility conditions, and without necessarily having a direct line of sight to the measured body part of subject 120, such as passing through certain types of obstructions or material barriers (e.g., clothing worn by subject 120, or a fabric or other material of a chair, sofa or mattress on which subject 120 is situated).

Processor 114 receives information or instructions from other components of system 110 and performs required data processing. For example, processor 114 receives and processes reflected radar signal 124 obtained by radar device 112 to derive an IBI measurement, as will be elaborated upon further hereinbelow.

Database 118 stores relevant information to be retrieved and processed by processor 114, such as radar signal data and associated information. Database 118 may be represented by one or more local servers or by remote and/or distributed servers, such as in a cloud storage platform.

Information may be conveyed between the components of system 110 over any suitable data communication channel or network, using any type of channel or network model and any data transmission protocol (e.g., wired, wireless, radio, WiFi, Bluetooth, and the like). For example, system 110 may store, manage and/or process data using a cloud computing model, and the components of system 110 may communicate with one another and be remotely monitored or controlled over the Internet, such as via an Internet of Things (IoT) network. The components and devices of system 110 may be based in hardware, software, or combinations thereof. It is appreciated that the functionality associated with each of the devices or components of system 110 may be distributed among multiple devices or components, which may reside at a single location or at multiple locations. For example, the functionality associated with processor 114 may be distributed between a single processing unit or multiple processing units. Processor 114 may be part of a server or a remote computer system accessible over a communications medium or network, such as a cloud computing platform. Processor 114 may also be integrated with other components of system 110, such as incorporated with radar device 112.

System 110 may optionally include and/or be associated with additional components not shown in FIG. 1, for enabling the implementation of the disclosed subject matter. For example, system 110 may include a user interface (not shown) for allowing a user to control various parameters or settings associated with the components of system 110, a display device (not shown) for visually displaying information relating to the operation of system 110, and/or a camera or imaging device (not shown) for capturing images of the operation of system 110.

The operation of system 110 will now be described in general terms, followed by specific examples. Radar device 112 transmits a (coherent) radar signal 122, such as a frequency-modulated continuous wave (FMCW) radar signal, to a body part of subject 120, and receives a corresponding reflected radar signal 124 containing information relating to micro-displacements in the skin associated with the cardiac cycle. Transmitted radar signal 122 may preferably be directed to a rear body area of subject 120, such as the back, but may also be directed to a frontal body area, such as the chest. Processor 114 receives the reflected radar signal 124 and measures a phase difference between the transmitted signal 122 and received signal 124 to determine the distance or range traversed by the propagating signal so as to extract the signal portion corresponding to reflections from subject 120 and eliminating noise and irrelevant signal components. For example, if an FMCW radar is employed, then a fast Fourier transform (FFT) may be applied to extract the portion of reflected signal 124 corresponding to the range at which subject 120 is located. The extracted signal portion (e.g., the output of the FFT, at the subject range) collected over predefined time intervals (e.g., 500 times per second) and consisting of an in-phase (I) component and a quadrature (Q) component, undergoes a linear filtering or linear mapping. In particular, the reflection radar signal portion with I-Q components is subject to a continuous wavelet transform (CWT) with complex valued wavelet coefficients, and having selected frequency and width parameters, typically limited within predefined ranges. For example, the applied complex-valued wavelet filter may be a complex-valued Morlet wavelet (e.g., with a center frequency between 5 and 30 Hz) or a Ricker wavelet, although other types of wavelets may also be utilized. An alternative form of linear filtering may be applied, such as a high pass filter, although a CWT may be preferable.

The resultant filtered signal substantially corresponds to a (complex-valued) ballistocardiograph signal providing a time-domain representation of the ballistic forces associated with cardiac activity, characterizing repetitive body movements caused by the ejection of blood into the vessels with each heartbeat. An initial heartbeat interval measurement may be derived according to the time displacement between repeating features of the complex-valued BCG signal. Further processing may be applied in order to enhance the BCG signal. The processing may include obtaining the absolute value of the complex signal (or otherwise mapping the complex number into a real number), removing the baseline (such as using a high-pass filter), and applying a gain control function (i.e., normalizing or equalizing the signal energy over time). The resultant real-valued BCG signal is characterized with cyclical distinctive peaks ("BCG peaks") which substantially coincide with "R peaks" of the QRS-complex in an ECG waveform to a substantially high degree of accuracy. IBI measurements may then be extracted based on the time displacement between consecutive recurring peaks in the resultant (real-valued) BCG signal, which substantially corresponds to the RR-interval of the corresponding ECG signal. It is appreciated that by obtaining IBI measurements directly from the time interval between successive peaks (or successive repeating features) in the derived BCG signal (substantially coinciding with the time interval between corresponding "R peaks" of an ECG waveform) without entailing a prior heart rate determination or frequency domain signal processing, additional metrics and statistics based on the IBI, e.g., standard deviation, may be determined with a higher degree of accuracy.

Figure 3:
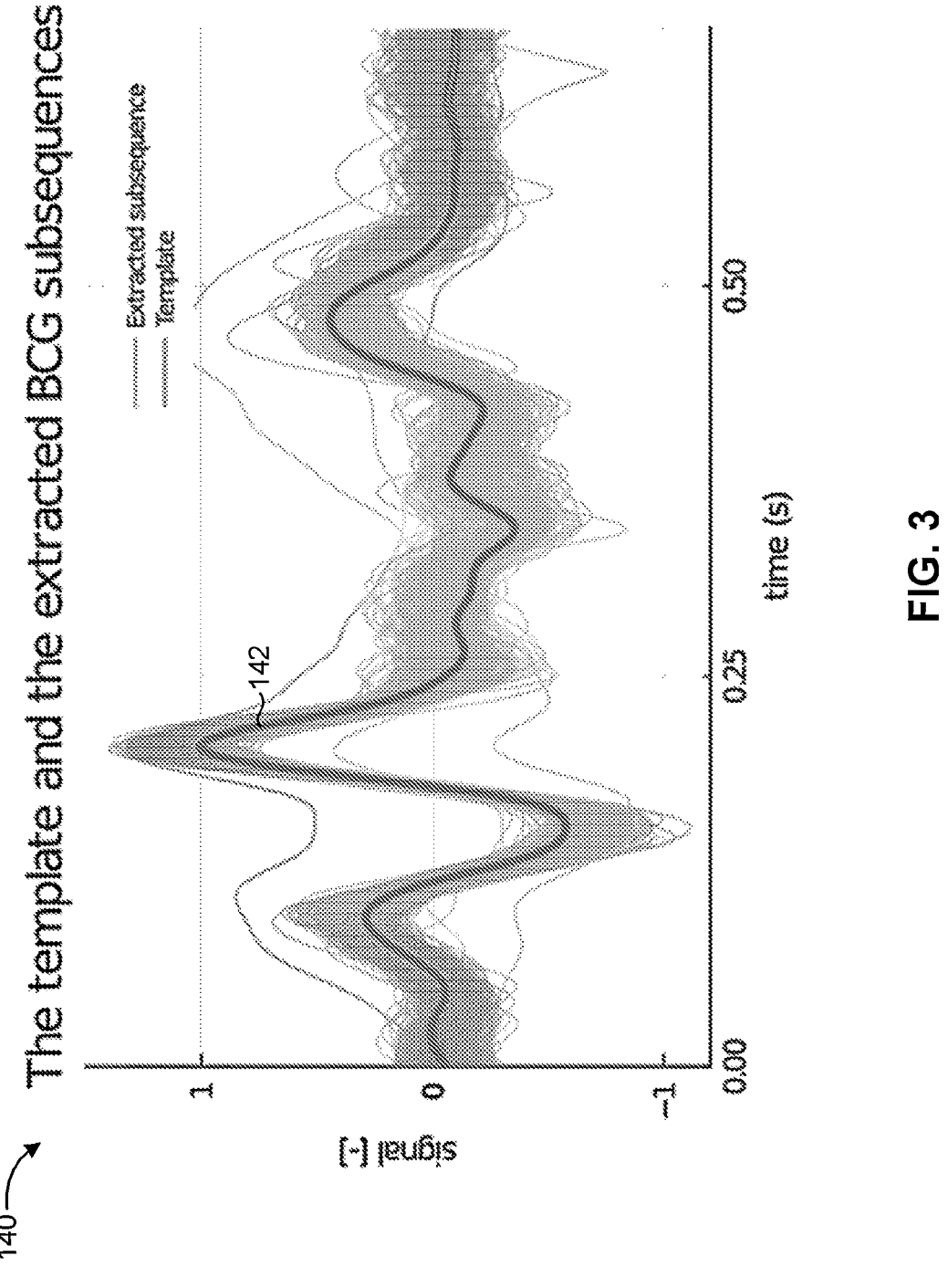
FIG. 3 illustrates a graph depicting individual heartbeat segments identified and extracted from a BCG signal derived in accordance with an embodiment of the present invention and superimposed on one another.

The accuracy may be enhanced further by identifying individual sections or segments of the BCG signal over a given duration. The features of an individual segment are unique to a given subject, although many individuals may share similar segment characteristics. Processor 114 may apply a matrix profile technique to identify the individual segments. Matrix profiling is a robust tool known in the art used for solving the dual problem of anomaly detection and motif discovery in time series data. Features of the identified segments may then be associated with the respective subject 120. An IBI measurement may subsequently be extracted based on the time displacement between successive identified signal segments. By considering entire segments of the BCG signal, rather than simply the individual peaks, a higher degree of accuracy may be obtained for the IBI measurement (e.g., accuracy on the order of milliseconds). Since the measured signal is an oscillation, there may be multiple candidate peaks close to one other. Reference is made to FIG. 3, which is a graph, referenced 140, illustrating individual heartbeat segments identified and extracted from a BCG signal derived in accordance with an embodiment of the present invention and superimposed on one another. Graph 140 depicts an exemplary BCG signal (reflected radar signal following digital signal processing steps) after individual heartbeat segments or subsequences have been identified and extracted (e.g., using a matrix profile technique) and displayed over one another. Waveform 142 (labelled "template") represents an average of the individual segments. A filtered radar signal represents the concatenation of a collection of heartbeat segments with some additional unknown time between them. When all the segments are extracted from the filtered radar signal and plotted as if they all started at the same time, as shown in graph 140, the variance of the heartbeats can be inspected. For example, the segments may indicate slight but consistent differences, which may be due to respiration and other factors. Graph 140 appears to show that the extracted heartbeat segments are highly similar but not absolutely identical. Furthermore, the peak locations may vary slightly and are not always exactly at the same point in relation to the rest of the identified segment, which may be due to respiration dynamics and other factors. Accordingly, identifying the location of an entire segment pattern generally provides a more robust and accurate fit than simply identifying individual peaks.

If matrix profiling is applied then some of the previous processing steps (e.g., mapping complex to real number, baseline removal, gain control) may potentially be eliminated. For example, the signal can be examined for a repeating complex valued pattern and use a measure of the distance (a real valued number) between two complex segments as an indicator. However, the application of baseline removal and gain control may facilitate the peak detection. Processor 114 may further compute heart rate variability (HRV) statistics from multiple IBI measurements of subject 120. The HRV statistics may provide indications for various physiological and pathological factors, such as: cardiovascular disease (e.g., myocardial infarction); neurological disorders; lifestyle habits (e.g., physical activity, alcohol consumption); physical attributes (e.g., age); neurophysiological issues (e.g., stress, fatigue, depression); and cardiac irregularities (e.g., cardiac arrhythmia).

Figure 2A:
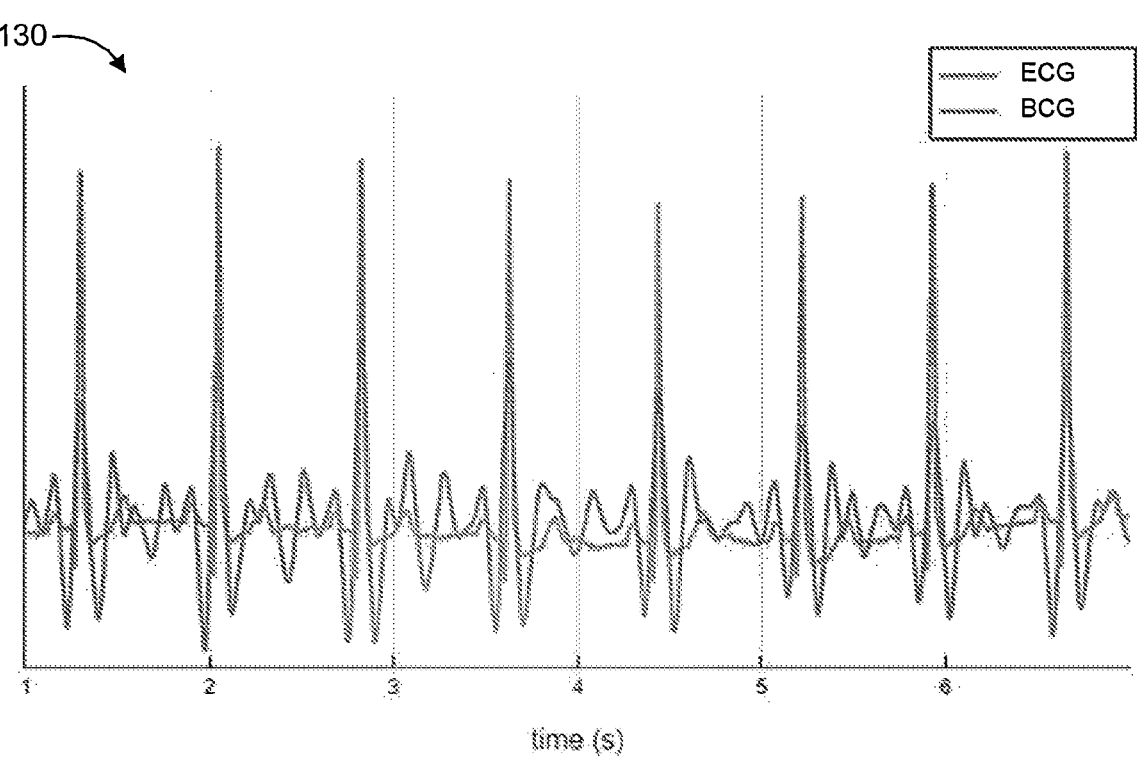
FIG. 2A illustrates a graph of a BCG signal derived in accordance with an embodiment of the present invention, along with a corresponding ECG waveform, plotted over an extended timespan.
Figure 2B:
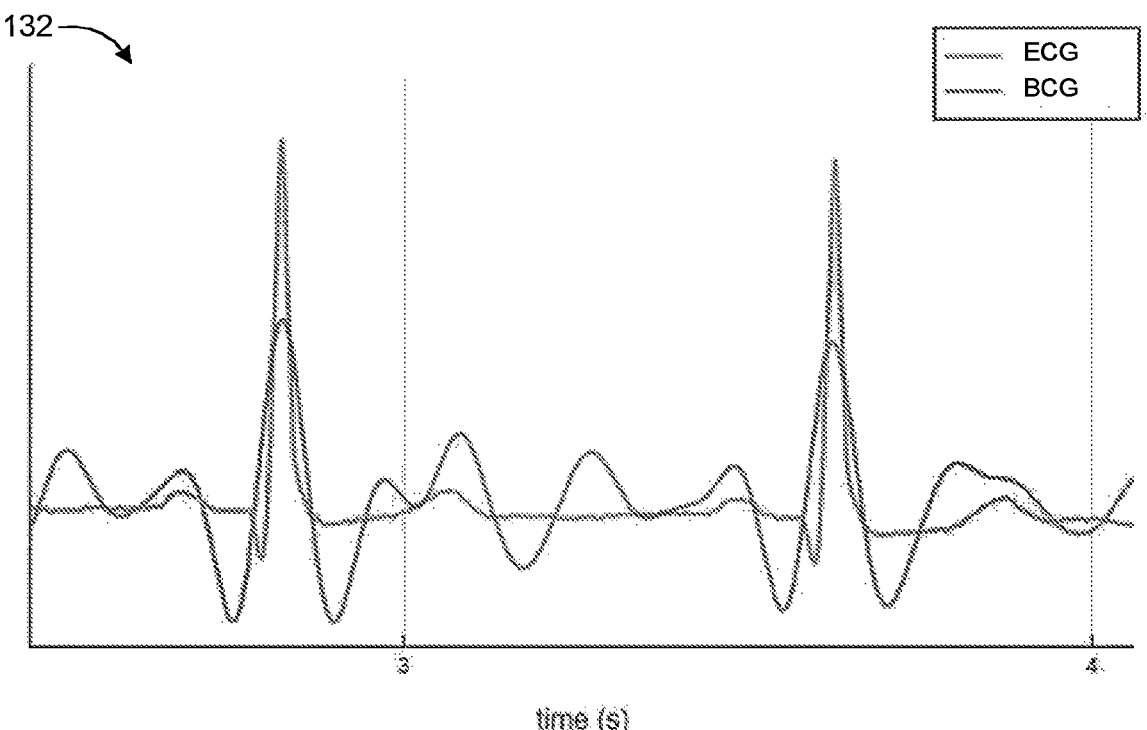
FIG. 2B illustrates a rescaled view of the graph of FIG. 2A depicting the BCG signal and corresponding ECG signal plotted over a shorter timespan.
Figure 2C:
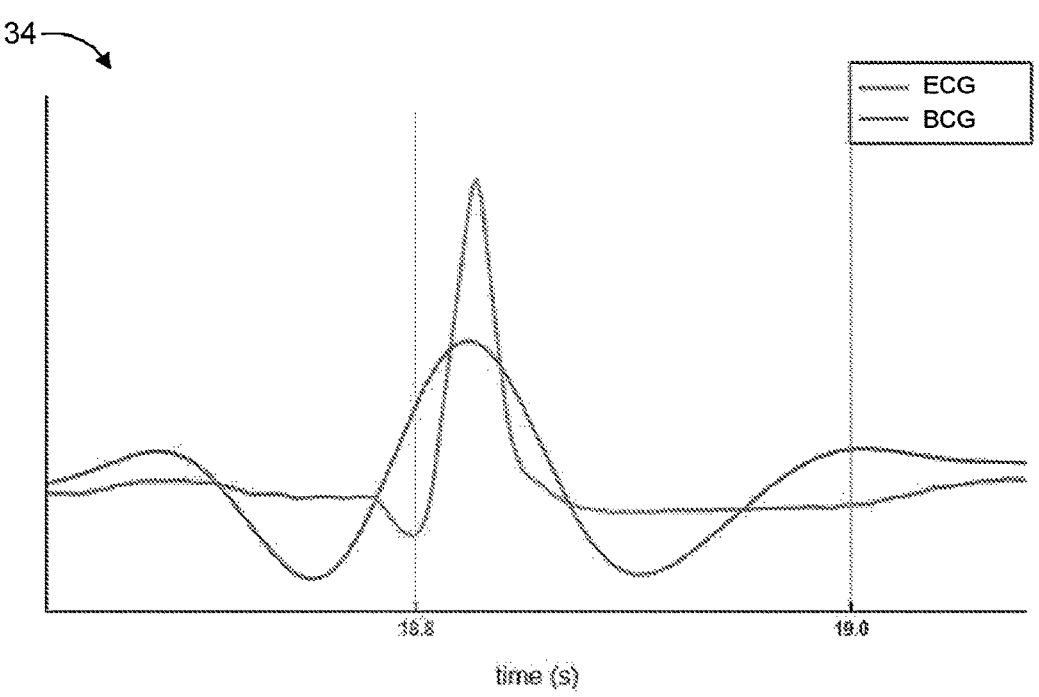
FIG. 2C illustrates a rescaled view of the graph of FIG. 2B depicting the BCG signal and corresponding ECG signal plotted over an even shorter timespan.
Figure 2D:
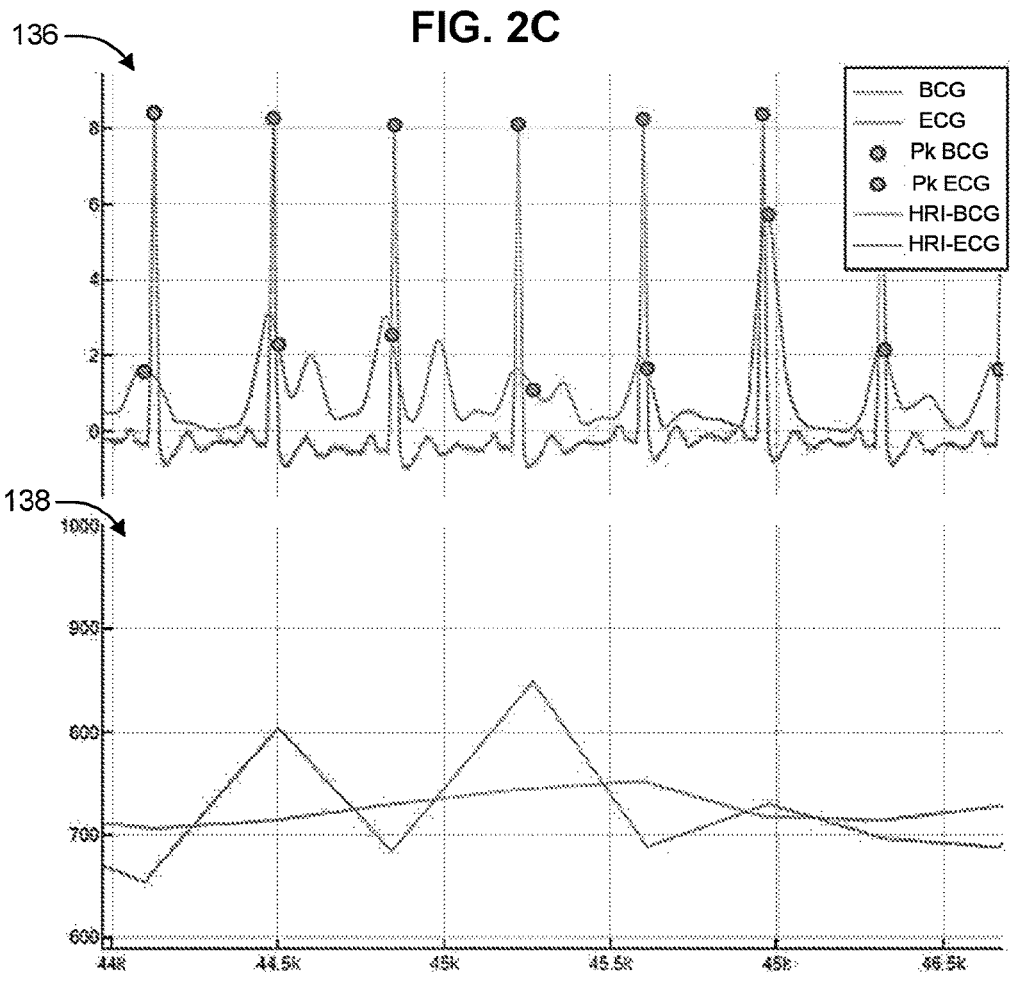
FIG. 2D illustrates a first graph depicting BCG signal peaks derived in accordance with an embodiment of the present invention, along with corresponding ECG signal peaks, and a second graph depicting IBI signals extracted from the BCG peaks and ECG peaks, respectively.

Reference is made to FIGS. 2A, 2B, 2C and 2D. FIG. 2A illustrates a graph, referenced 130, of a BCG signal derived in accordance with an embodiment of the present invention, along with a corresponding ECG waveform, plotted over an extended timespan. FIG. 2B illustrates a rescaled view 132 of the graph of FIG. 2A depicting the BCG signal and corresponding ECG signal plotted over a shorter time-span. FIG. 2C illustrates a rescaled view 134 of the graph of FIG. 2B depicting the BCG signal and corresponding ECG signal plotted over an even shorter time-span. FIG. 2D illustrates a first graph 136 depicting BCG signal peaks derived in accordance with an embodiment of the present invention, along with corresponding ECG signal peaks, and a second graph 138 depicting IBI signals extracted from the BCG peaks and ECG peaks, respectively. It is evident that the BCG signal (depicted following the application of a matrix profile) substantially overlaps the ECG signal, particularly with regard to the peak portion, as the BCG peak occurs substantially concurrent to the ECG peak. Accordingly, the timing of individual heartbeats can be effectively identified from the BCG signal. It can also be seen from graph 138 that the IBI value derived from the BCG signal when averaged over time substantially corresponds to the IBI value derived from the ECG signal.

Figure 4:
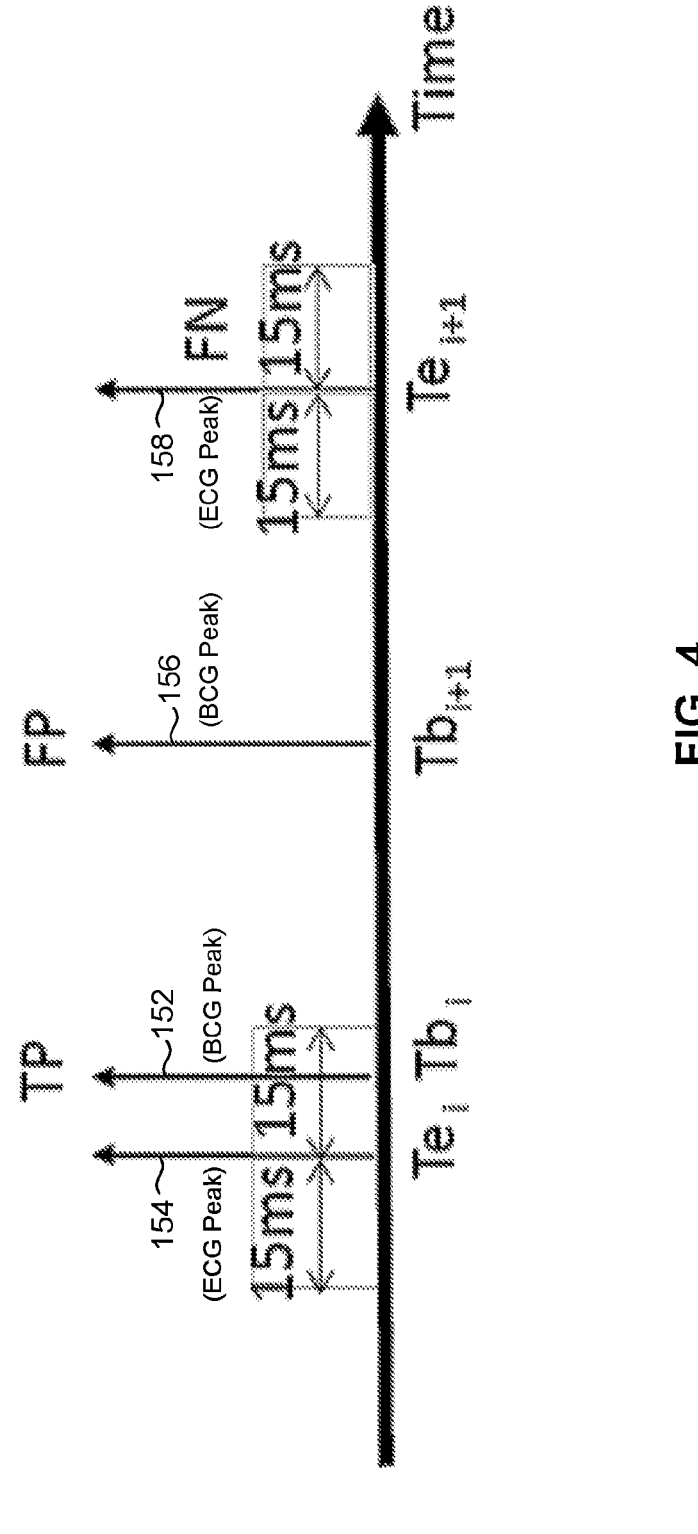
FIG. 4 illustrates a timing graph comparing heartbeat measurements derived according to embodiments of the present invention with heartbeats derived from ECG waveform R-peaks.

The accuracy of IBI measurements obtained from the BCG signal (derived from the reflected THz radar signal) can be validated by comparing the heartbeats timing with the R-peaks of an ECG waveform of the respective subject. Reference is made to FIG. 4, which illustrates a timing graph, referenced 150, comparing heartbeat measurements derived according to embodiments of the present invention with heartbeats derived from ECG waveform R-peaks. A true positive (TP) is defined as an ECG signal R-peak timepoint (Te) for which there is a corresponding BCG signal peak (Tb) occurring in proximity of 15 milliseconds (ms) or less to Te (i.e., |Tb−Te|<15 ms). For example, BCG peak value 152 (at timepoint $Tb_i$) in timing graph 140 represents a true positive (TP) heartbeat measurement, as BCG peak 152 occurs less than 15 ms following ECG signal peak value 154 (at timepoint $Te_i$). A false positive (FP) is defined as a BCG signal peak (Tb) timepoint for which there is no ECG signal R-peak timepoint (Te) occurring in a proximity of 15 ms interval (i.e., |Tb−Te|<15 ms). For example, −BCG peak value 156 (at timepoint $Tb_{i+1}$) in timing graph 150 represents a false positive (FP) heartbeat measurement, as no ECG peak occurs within 15 ms before or after BCG peak 156. A false negative (FN) is defined as an ECG signal R-peak (Te) timepoint for which there is no BCG signal peak occurring in a proximity of 15 ms interval (i.e., |Tb−Te|<15 ms). For example, ECG peak value 158 (at timepoint $Te_{i+1}$) in timing graph 150 represents a false negative (FN) heartbeat measurement, as no BCG peak occurs within 15 ms before or after ECG peak 158. Since the IBI represents the time difference between consecutive heartbeats, a delay between an ECG peak and a BCG peak can be effectively ignored (i.e., (t1−t2)=((t1+d)−(t2+d)). This delay may include both a physiological interpretation (the measured signal is not an electrical signal but rather a mechanical signal that is an outcome of the electrical one), as well as an interpretation (e.g., the timing mechanism of the ECG device may operate at the same frequency as that of the radar device but there may nevertheless be a relative delay between them for technical reasons).

Figure 5:
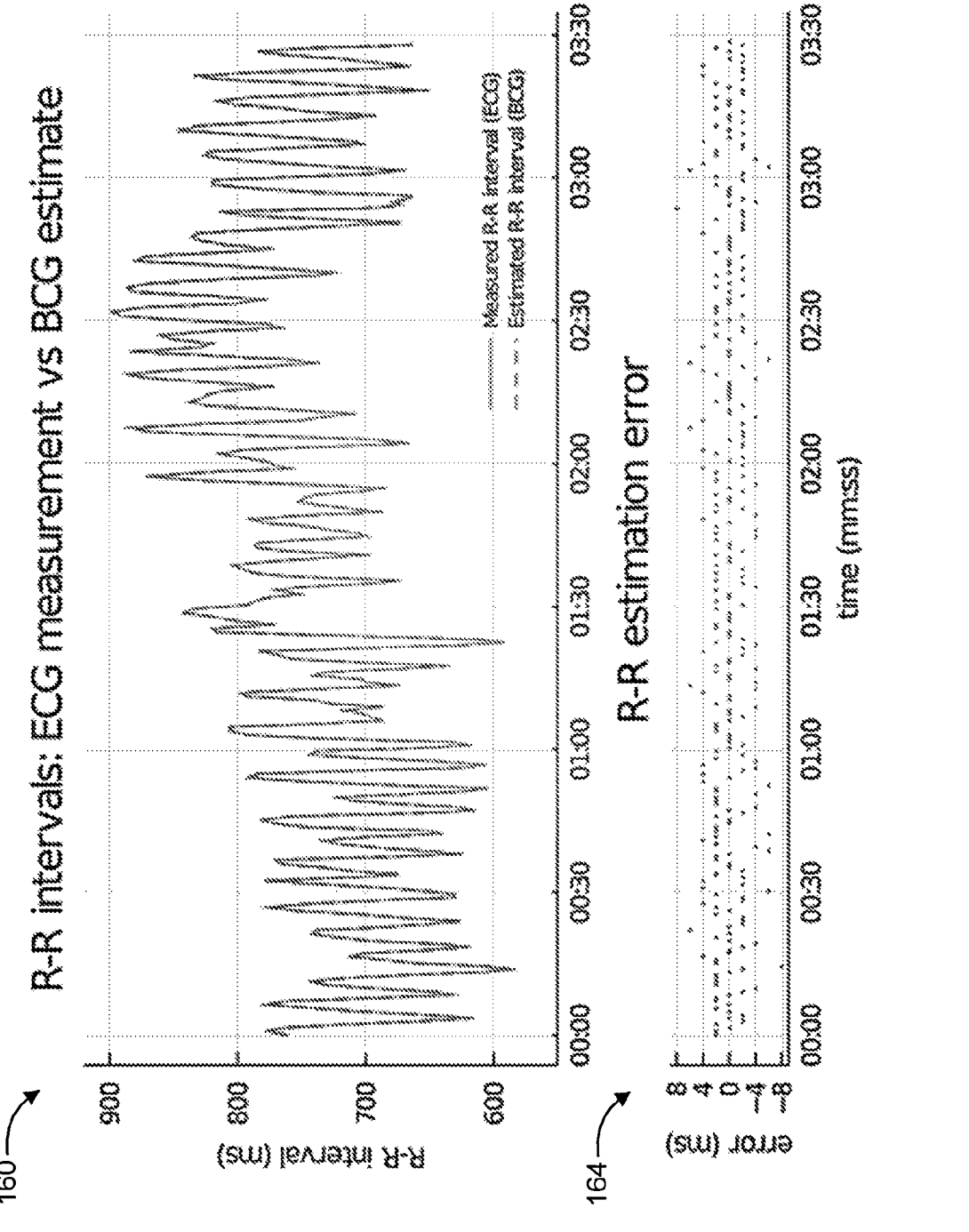
FIG. 5 illustrates a timing graph plotting peak to peak intervals measured from an ECG signal and from a BCG signal derived according to embodiments of the present invention.

Another comparison with ECG derived IBI measurements is shown in FIG. 5, which illustrates a timing graph, referenced 160, plotting peak to peak intervals measured from an ECG signal and from a BCG signal derived according to embodiments of the present invention. The R-R intervals (R-peak to R-peak) obtained from an ECG signal is depicted with a solid line, whereas the peak-to-peak intervals measured in the BCG signal is depicted with a dashed line. Graph 160 plots the peak-to-peak intervals of each medium as a function of time. The ECG measurements and the BCG measurements exhibit a substantial visual overlap, indicating that no heartbeat was overlooked, and that the relative error is extremely low. A corresponding graph 164 plots the error or discrepancies in the peak-to-peak intervals measured from the ECG signal vs the corresponding intervals measured from the BCG signal as a function of time-pair of successive heartbeats has a measured interval (ECG) and an estimated interval (radar). A dot is plotted at the time when the heartbeat occurs (the position on the x-axis, minutes and seconds into the experiment) and at the error between the real interval and estimated interval (y-axis, milliseconds). Graph 164 illustrates horizontal "bands" at 2 ms steps (i.e. errors are either −8 ms, −6 ms, −4 ms . . . , 8 ms), because both the radar and the ECG device measure with a sampling time of 2 ms (i.e. their sampling rates are 500 Hertz).

It is appreciated that the system and method of the present invention may provide reliable heartbeat interval and heart-rate variability detection with a high degree of accuracy, such as in the range of several milliseconds, without requiring devices or components to be in direct physical contact with the subject. Furthermore, the subject does not need to be directly visible to the radar device, which may operate under poor visibility or low light conditions, under obstructions or interference, and from different angles in relation to the subject (e.g., from in front or from behind). The disclosed system does not require costly equipment and has relatively few components, and is relatively straightforward to operate and maintain. The derived ballistocardiogram signal correlates substantially with a standard ECG waveform, and may be more informative in certain application as it reflects the physiological-mechanical response of the heart and body rather than merely the electric signals detected by ECG monitors. Furthermore, the derived BCG signal may be converted into a corresponding ECG signal and visually displayed to a medical practitioner. For example, a corresponding ECG signal may be obtained using suitable mapping techniques, or by selecting an optimal match from a collection of prestored signals, which may be linked to the same subject or other similar subjects, such as by using feature matching algorithms and/or machine learning processes. In general, a medical practitioner (e.g., cardiologist) may be presented with a suitable cardiac signal format (radar derived BCG signal or corresponding ECG signal) in accordance with situational and/or personal preferences, in order to facilitate or augment a diagnosis or treatment of the subject. BCG analysis by a medical practitioner may be similar to the use of stethoscopes for heart diagnosis. By nature, a human-hearing based diagnosis device is a "subjective" measure, as which the radar-derived BCG signal may also be considered.

The disclosed system and method can be used for various applications, ranging from home healthcare to medical diagnosis. Some examples include: sleep stage classification; detecting levels of drowsiness, nervousness, excitement, and heartrate (HR); and detection of medical abnormalities such as atrial fibrillation, missing or extra heart beats, and the like.

Figure 6:
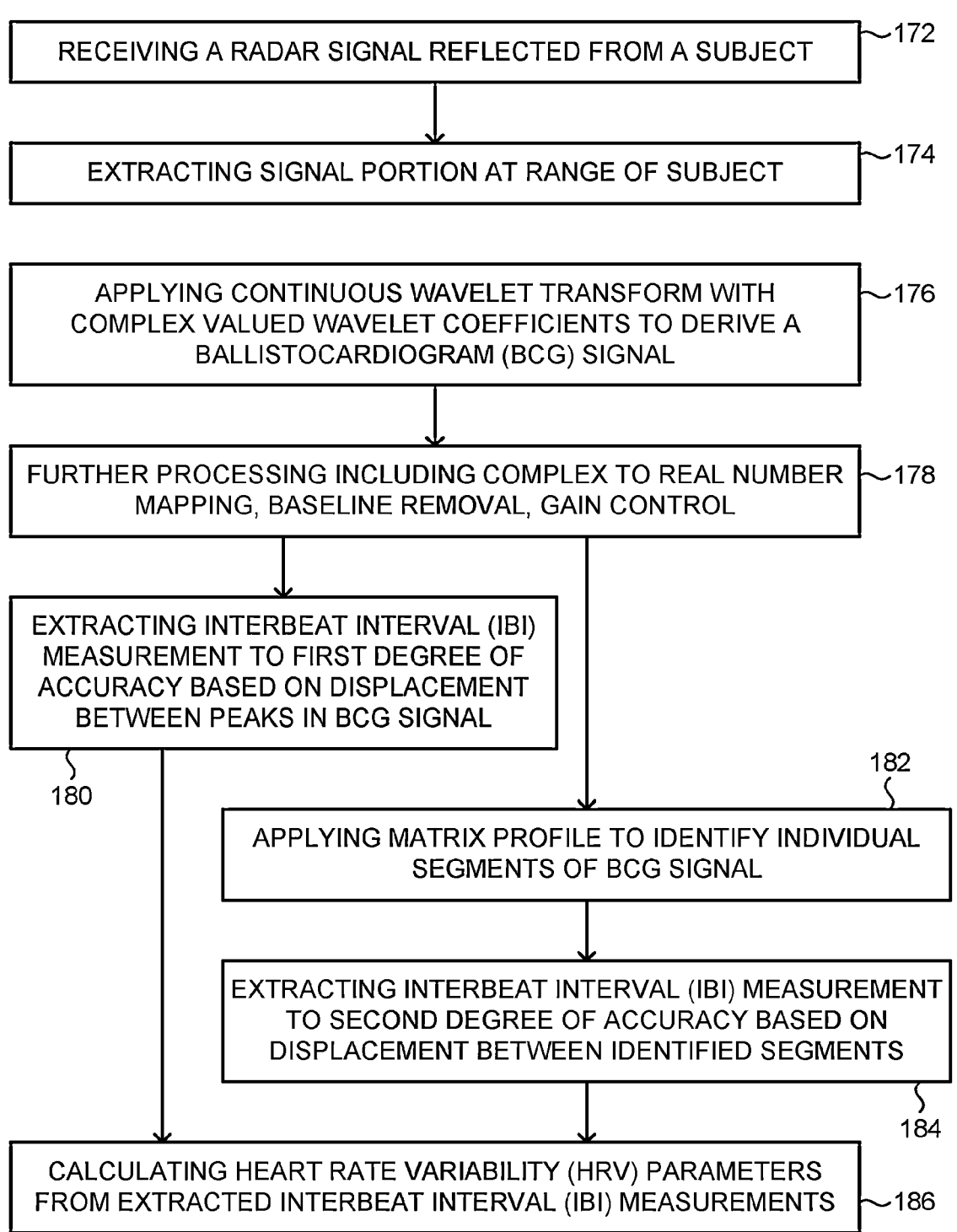
FIG. 6 is a block diagram of a method for deriving an interbeat interval measurement, operative in accordance with an embodiment of the present invention.

Reference is now made to FIG. 6, which is a block diagram of a method for deriving an interbeat interval measurement, operative in accordance with an embodiment of the present invention. In procedure 172, a radar signal reflected from a subject is received. Referring to FIG. 1, radar device 112 transmits a radar signal 122 and receives a reflected radar signal 124 reflected back from a body tissue of subject 120. The received reflected radar signal 124 contains information relating to skin tissue micro-displacements linked to cardiac activity of subject 120. Reflected radar signal 124 may be obtained in a contactless manner, and without requiring a direct line of sight to the measurement body region.

In procedure 174, a signal portion at the range of the subject is extracted. Referring to FIG. 1, processor 114 filters reflected radar signal 124 to tune the signal to the correct range of subject 120. Processor 114 filters out noise and signal elements at nonrelevant ranges based on signal phase differences which correlates with distance. If transmitted and reflected radar signals 122, 124 are FMCW radar signals then processor 114 may apply a fast Fourier transform (FFT) to extract the signal portion corresponding to the subject range (i.e., to identify the relevant "FFT bin").

In procedure 176, a continuous wavelet transform with complex valued wavelet coefficients is applied to derive a BCG signal with peaks representative of subject heartbeats. Referring to FIG. 1, processor 114 applies a linear filtering to the extracted signal portion of reflected radar signal 124 using a continuous wavelet transform (CWT) with complex valued wavelet coefficients, such as a Morlet wavelet or a Ricker wavelet, having selected parameters in predefined ranges. The output substantially corresponds to a ballisto-cardiograph signal representative of cardiac activity of subject 120.

In procedure 178, the filtered signal is processed, including complex to real number mapping, baseline removal and gain control. Referring to FIG. 1, processor 114 applies further processing to enhance the BCG signal. The processing may include the steps of mapping complex to real number values in the signal (e.g., by taking the absolute value of the complex signal), removing the baseline (e.g., using a high-pass filter), and applying a gain control function (normalizing or equalizing the signal energy over time). The resultant BCG signal is characterized with cyclical peaks which substantially coincide with the R-peaks of a corresponding ECG signal of the subject 120. Referring to FIGS. 2B and 2C, graphs 132 and 134 visually illustrate the correspondence of the peaks in the derived BCG signal with the R-peaks in an ECG signal of the subject.

In procedure 180, at least one interbeat interval (IBI) measurement is extracted to a first degree of accuracy based on the displacement between peaks in the derived BCG signal. Referring to FIG. 1, processor 114 extracts one or more IBI measurements of subject 120 based on the displacement between consecutive peaks in the BCG signal, which substantially correspond to the RR-interval of a corresponding ECG signal. Referring to FIG. 2D, graph 138 visually illustrates the IBI values derived from the peak to peak distances in the BCG signal of subject, substantially corresponding to IBI values obtained from the R-peak to R-peak (RR) distances in an ECG signal of the subject.

In procedure 182, a matrix profile is applied to identify individual segments of the BCG signal. Referring to FIG. 1, processor 114 apply a matrix profile technique to identify individual segments in the BCG signal, and associates features of the identified segments with subject 120.

In procedure 184, at least one interbeat interval (IBI) measurement is extracted to a second degree of accuracy based on the displacement between identified segments of the derived BCG signal. Referring to FIG. 1, processor 114 extracts one or more IBI measurements of subject 120 based on the displacement between identified segments of the BCG signal. By considering entire segments of the BCG signal, rather than simply the individual peaks, a higher degree of accuracy may be obtained for the IBI measurement (e.g., on the order of milliseconds).

In procedure 186, at least one heart rate variability (HRV) parameter is determined from extracted interbeat interval (IBI) measurements. Referring to FIG. 1, processor 114 determines HRV parameters of subject 120 from the IBI measurements extracted in procedure 178 and/or procedure 182. The HRV statistics may provide indications for various physiological and pathological factors of subject 120.

The method of FIG. 6 is generally implemented in an iterative manner, such that at least some of the procedures are performed repeatedly, in order to provide for a dynamic derivation of IBI measurements and HRV statistics of one or more subjects in real-time.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. A method for measuring interbeat interval (IBI) of a subject, the method comprising:
   receiving a THz or millimeter-wave reflection radar signal reflected from the subject;
   sampling the reflection radar signal and extracting a signal portion at a range of the subject, the signal portion consisting of an in-phase (I) component and a quadrature (Q) component;
   filtering the signal portion by applying a complex valued continuous wavelet transform (CWT) with a center frequency between 5 Hz and 30 Hz, to derive a time domain ballistocardiograph (BCG) signal including frequency components between 5 Hz and 30 Hz and having with cyclically repeating features; and
   determining at least one first heartbeat interval measurement based on a time displacement between consecutive repeating features of the derived BCG signal.

2. The method of claim 1, further comprising:
   identifying segments of the BCG signal over a selected time duration using a matrix profile technique; and
   determining at least one second heartbeat interval measurement based on a time displacement between successive identified segments.

3. The method of claim 1, further comprising processing the BCG signal by at least one processing step selected from the group consisting of:
   applying a complex number to real number mapping;
   removing a baseline using a high-pass filter; and
   applying a gain control function.

4. The method of claim 1, wherein the radar signal is a frequency-modulated continuous-wave (FMCW) radar signal.

5. The method of claim 4, wherein extracting a signal portion at a range of the subject comprises applying a fast Fourier transform (FFT) to the FMCW radar signal.

6. The method of claim 1, further comprising deriving a heartrate variability (HRV) measurement from variations of a plurality of heartbeat interval measurements extracted from the BCG signal.

7. The method of claim 1, further comprising displaying an electrocardiogram (ECG) signal corresponding to the derived BCG signal, the ECG signal obtained using at least one of: a mapping technique; a feature matching process; and a machine learning process.

8. A system for measuring interbeat interval (IBI) of a subject, the system comprising:
   a radar device, configured to receive a THz or millimeter-wave reflection radar signal reflected from the subject; and
   a processor, configured to:
   receive a sampling of the reflection radar signal and extract a signal portion at a range of the subject, the signal portion consisting of an in-phase (I) component and a quadrature (Q) component;
   filter the signal portion by applying a complex valued continuous wavelet transform (CWT) with a center frequency between 5 Hz and 30 Hz, to derive a time domain ballistocardiograph (BCG) signal including frequency components between 5 Hz and 30 Hz and having cyclically repeating features; and
   determine at least one first heartbeat interval measurement based on a time displacement between consecutive repeating features of the derived BCG signal.

9. The system of claim 8, wherein the processor is further configured to;
   identify segments of the BCG signal over a selected time duration using a matrix profile technique; and determine at least one second heartbeat interval measurement based on a time displacement between successive identified segments.

10. The system of claim 8, wherein the processor is configured to process the BCG signal by at least one processing step selected from the group consisting of:

applying a complex number to real number mapping;

removing a baseline using a high-pass filter; and applying a gain control function.

11. The system of claim 8, wherein the radar device comprises a remote non-invasive radar device comprising:

at least one radar transmitter, configured to transmit a radar signal to a body tissue of the subject; and at least one radar receiver, configured to receive a THz or millimeter-wave reflection of the transmitted radar signal reflected from the body tissue of the subject.

12. The system of claim 8, wherein the radar signal is a frequency-modulated continuous-wave (FMCW) radar signal.

13. The system of claim 12, wherein the processor is configured to extract a signal portion at a range of the subject by applying a fast Fourier transform (FFT) to the FMCW radar signal.

14. The system of claim 8, wherein the processor is further configured to derive a heartrate variability (HRV) measurement from variations of a plurality of heart beat interval measurements extracted from the BCG signal.

15. The system of claim 8, further configured to display an electrocardiogram (ECG) signal corresponding to the derived BCG signal, the ECG signal obtained using at least one of: a mapping technique; a feature matching process; and a machine learning process.

\* \* \* \* \*